United States Patent

Reitz

Patent Number: 5,902,286
Date of Patent: May 11, 1999

[54] ROLLING CATHETER OR MEDICAL DEVICE FOR STERILE ACCESS TO BLADDER URINE

[76] Inventor: James C. Reitz, 44615 Marguerite Ct., La Quinta, Calif. 92253

[21] Appl. No.: 09/057,085

[22] Filed: Apr. 8, 1998

Related U.S. Application Data

[60] Provisional application No. 60/044,832, Apr. 25, 1997.

[51] Int. Cl.⁶ ..................................................... A61M 5/00
[52] U.S. Cl. ........................................... 604/271; 604/264
[58] Field of Search ..................... 604/280, 264, 604/266, 329, 171, 181, 317, 327, 164, 165, 158, 161, 162, 163, 403, 331, 332, 271

[56] References Cited

U.S. PATENT DOCUMENTS

| | | | |
|---|---|---|---|
| 3,084,693 | 4/1963 | Cathcart | 604/271 |
| 3,866,601 | 2/1975 | Russell | 600/114 |
| 3,908,635 | 9/1975 | Viek . | |
| 3,908,663 | 9/1975 | Viek . | |
| 4,072,146 | 2/1978 | Howes | 600/487 |
| 4,109,659 | 8/1978 | Sheridan . | |
| 4,871,358 | 10/1989 | Gold | 604/271 |
| 4,911,691 | 3/1990 | Aniuk et al. | 604/164 |
| 5,149,330 | 9/1992 | Brightbill | 604/280 |
| 5,322,513 | 6/1994 | Walker | 604/161 |
| 5,478,331 | 12/1995 | Heflin et al. | 604/283 |
| 5,749,857 | 5/1998 | Cuppy | 604/164 |

FOREIGN PATENT DOCUMENTS

WO 92/21399 of 1992 WIPO .

*Primary Examiner*—Wynn Wood Coggins
*Assistant Examiner*—LoAn H. Thanh

[57] ABSTRACT

A medical device for sterile access to bladder urine having a hollow handle 26 with a guard 24 and a radially disposed group of tines or guide 22. A flexible tube 28 passes through the handle and is attached at the remote end of the handle.

1 Claim, 3 Drawing Sheets

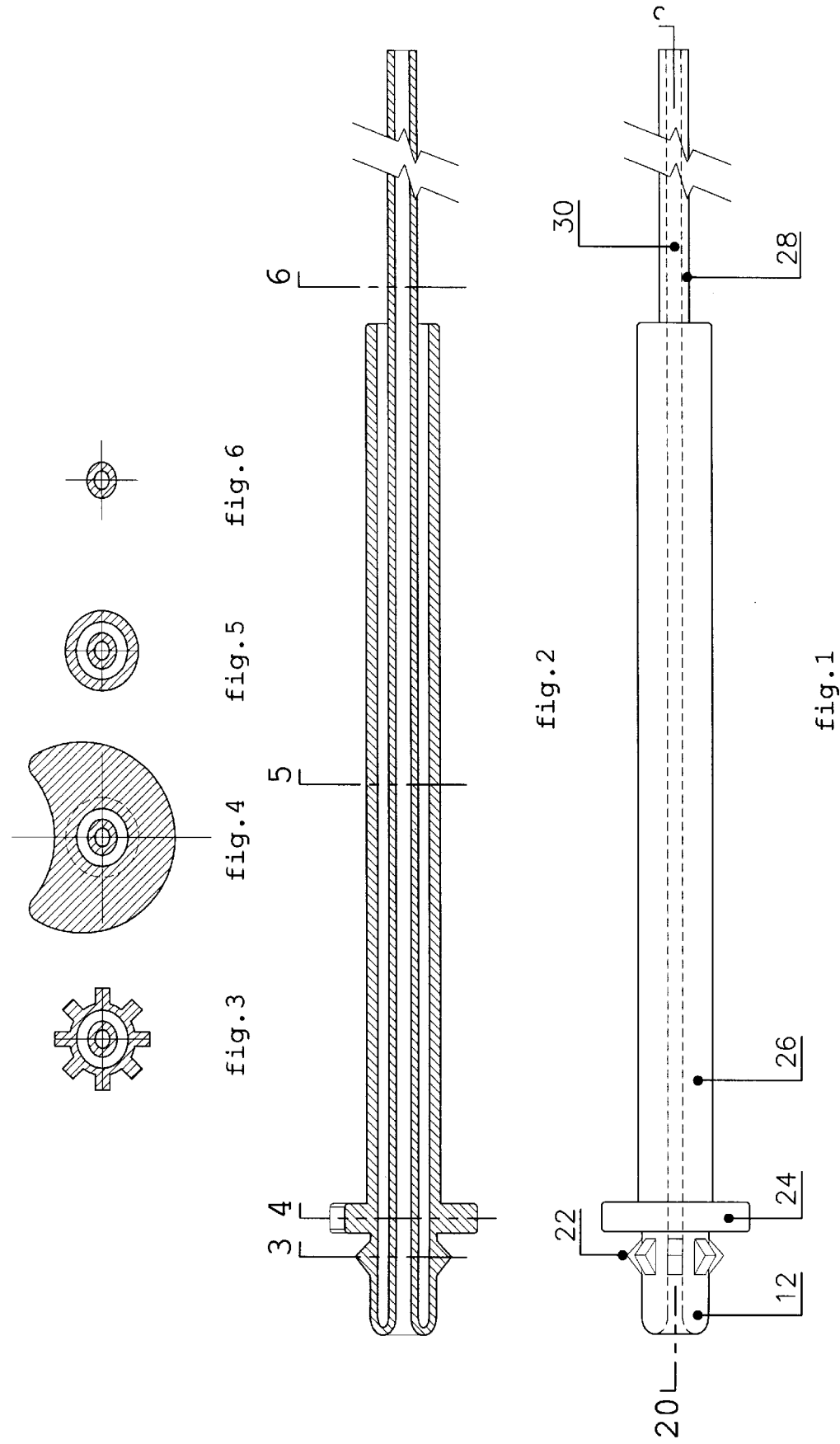

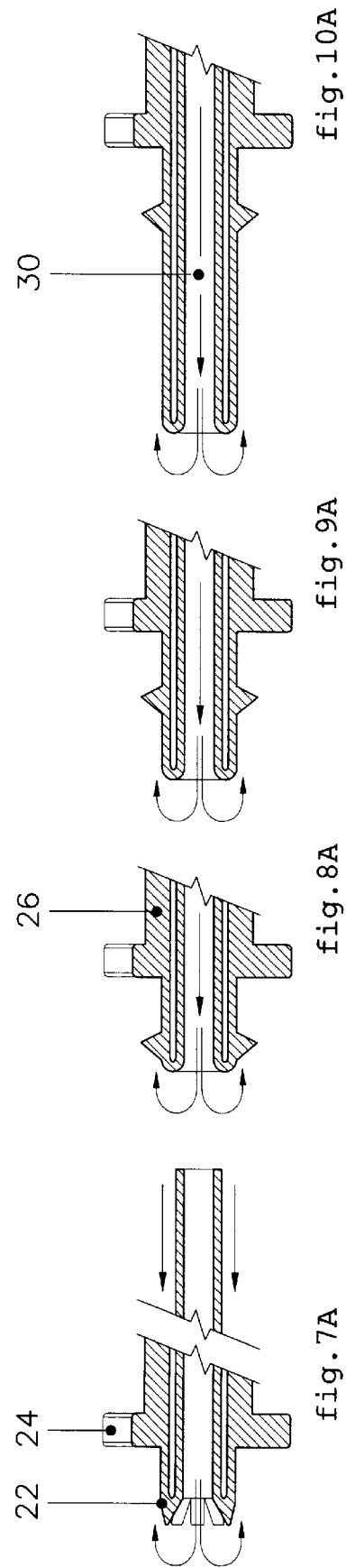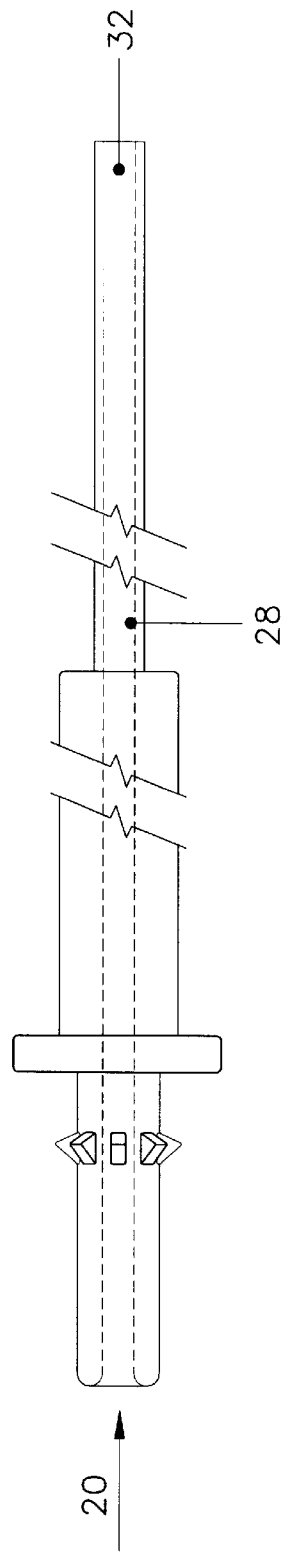

ROLLING CATHETER OR MEDICAL DEVICE FOR STERILE ACCESS TO BLADDER URINE

This application claims benefit of provisional application 60/044832 filed Apr. 25, 1997.

BACKGROUND

1. Field of Invention

This invention relates to safely sampling urine from the urinary bladder.

2. Description of Prior Art

Physicians order a vast number of urine tests every day. Many of these tests are routine and most seek information of chemical or of hormonal nature. Such tests can reliably be performed on voided urine specimens. The urine is simply gathered in an open cup. Patients can do their own specimen collecting and sterile precautions are unnecessary. A few contaminating bacteria will not affect the test results.

But when the problem of managing urinary infection arises, voided specimens become unreliable. Bacterial organisms living in the genital area will contaminate voided urine specimens and lead to erroneous culture findings. Wrong organisms are treated; false antibiotic sensitivity studies are obtained; and uninfected patients are unnecessarily treated.

Thus the bacteriologic study of urine requires a different method of urine sampling.

Originally and even in practice today many suspected infections of the urinary tract are studied by passing a sterile straight hollow tube (catheter) directly into the bladder to obtain urine. Bacterial contamination of urine specimens can be avoided by the use of a catheter. With some basic skill and a little experience, one can obtain an uncontaminated urine sample using this straight catheter method.

Unfortunately, as the catheter advances, it slides through a zone of bacterial contamination in the distal urethra before entering the bladder. The catheter then carries bacteria into the bladder where seeding occurs. Patients who did not have bladder infection will often develop bladder infection following and as a result of straight catheterization.

Recently inventors created several variations of the catheter which are intended to prevent bladder seeding with organisms from the lower urethra. U.S. Pat. No. 3,908,663 A dated Sep. 30, 1975 to N. F. Viek, and International patent WO 92/21399A dated Dec. 10, 1992 to R. Feliziani and M. L. Jake use a progressively unrolling separate membrane to isolate urethral walls from the advancing catheter. Similarly U.S. Pat. No. 4,106,659 dated Aug. 29, 1978 to D. Sheriden describes an unrolling separate membrane. Sheriden's membrane is unrolled by externally applied fluid pressure.

While membrane catheters do have the potential to avoid bladder contamination, they have not received general acceptance. These devices are complicated to use and expensive to manufacture. They require training and technical skills which are not always available in the working clinical laboratory.

Another variation of the catheter intended to prevent bladder seeding was patented by V. F. Viek (U.S. Pat. No. 3,908,635 dated Sep. 30, 1975). He describes a simplified catheter comprising a disc with an opening and attached flexible tube which passes through the opening and "everts" into the urethra.

This design seems preferable to the complexity of a separate membrane. Because the advancing tube forms its own encasement, the everting feature substitutes for a separate membrane. And nowhere does a sliding surface contact a contaminated area.

Clearly Viek's simplified catheter contains a good basic idea for safely traversing the urethral canal. Yet this simplified design functions poorly as a clinical tool and it suffers from a number of disadvantages:

(a) The disc is too small to adequately control the device.
(b) Placing the disc against the skin of the perineum conceals the opening to the urethra, requiring blind catheterization.
(c) Pressing the disc against the perineum compresses and traps folds of urethral mucosa making penetration difficult and sometimes painful.
(d) The urine specimen dribbles uncontrolled from the catheter and is subject to spillage and contamination.
(e) Coughing or laughing by the patient will lead to uncontrollable spraying of urine.
(f) A sterile procedure tray of equipment is needed to supplement this catheter.
(g) An operator trained in sterile technique is needed to supplement this catheter.

OBJECTS AND ADVANTAGES

Several objects and advantages of the present invention are:

(a) to provide a well supported and controlled device allowing incremental changes of catheter direction, pressure, and rate of penetration;
(b) to gently separate mucosal folds at the urethral opening and permit easy penetration by the catheter;
(c) to prevent excessive penetration of the urethra without blocking visualization of the meatus;
(d) to collect urine without bacterial contamination of the specimen;
(e) to collect urine without bacterial contamination of the bladder;
(f) to avoid spillage by use of a controlled drainage tube;
(g) to provide a safe means for introducing medications into the bladder;
(h) to decrease the level of training required for urine sampling;
(i) to decrease the amount of equipment required for urine sampling;
(j) to decrease the cost of urine sampling.

Additional objects and advantages will become apparent from a consideration of the ensuing description and drawings.

DESCRIPTION OF DRAWINGS

FIG. 1 is a perspective side view of my invention before use but with the guide tines extended.

FIG. 2 is a longitudinal cross section of FIG. 1.

FIG. 3 is a view of the inlet end and shows a guide.

FIG. 4 is a cross section through a guard.

FIG. 5 is a cross section through a handle.

FIG. 6 is a cross section through a tube.

FIGS. 7, 8, 8A, 9, 9A, 10, 10A demonstrate continued advance of the tube resulting in continued growth of combined tube.

FIG. 11 shows an extended catheter.

LIST OF REFERENCE NUMERALS

Figure 8:
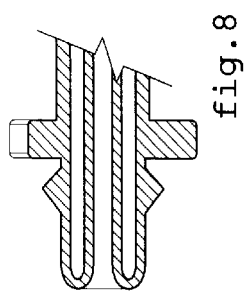
FIGS. 7 & 8 demonstrate advance of inner tube with resultant opening by guide and lengthening of adjacent catheter. Guide tines extend between FIG. 7A and FIG. 8A.

12 Junction of inner tube and outer tube
14 Innertube
16 Outer tube
18 Combined tube
20 Specimen entrance
22 Guide
24 Guard
26 Handle
28 Free end of inner tube
30 Cavity of tube
32 Specimen exit

SUMMARY

My invention is a medical device to safely access urine from the urinary bladder. The design will permit sampling into either sterile or non-sterile laboratory containers. Bacterial contamination of the bladder and of the urine specimen are both avoided. Penetration of the urethra is facilitated by a unique method of exposure.

DESCRIPTION FIGS. 1 TO 11

Typical embodiment of this invention is illustrated in FIGS. 1 and 2 (side views). A flexible cylindrical hollow tube 28 having a first end defined by the specimen exit (32) is passed through a rigid hollow handle 26 and attached at the junction (12) of the inner tube and outer tube where the specimen entrance or inlet is located at the second end of the hollow tube (28). Urine exits at the specimen exit 32 and the free tube which extends beyond the handle must be at least 7 cm longer than the handle. Outside diameter of the tube is approximately 0.5 cm. The tube must endure folding several times without fracture.

A guide 22 is placed at the inlet end of the device. FIG. 3 (end view) demonstrates the radially positioned tines of this structure. The tines swing outward from the center line of the device when the free tube is advanced and fabric transfers from the inner tube to the outer tube (i.e., the free tube becomes the inner tube to form a double walled catheter).

A guard 24 surrounding the outer tube is located near the inlet end specimen entrance end. FIG. 4 is a cross-section of that feature showing its relative area and shape.

FIG. 5 is a cross-section through the handle and shows the relative sizes of handle and contained tube. The tube is advanced by grasping with fingers and manually applying force in the direction of the handle.

FIG. 6 is a cross-section of the tube.

Figure 9:
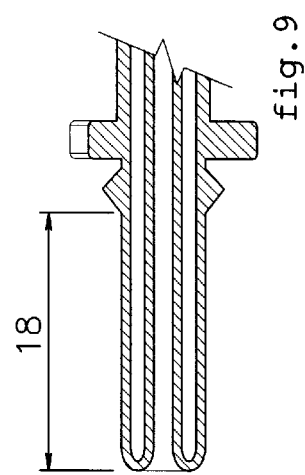
Figure 10:
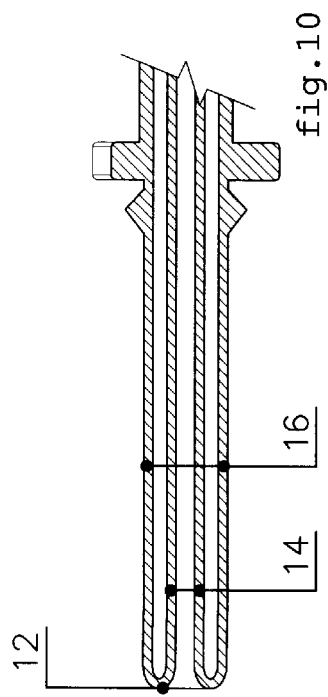
Figure 7:
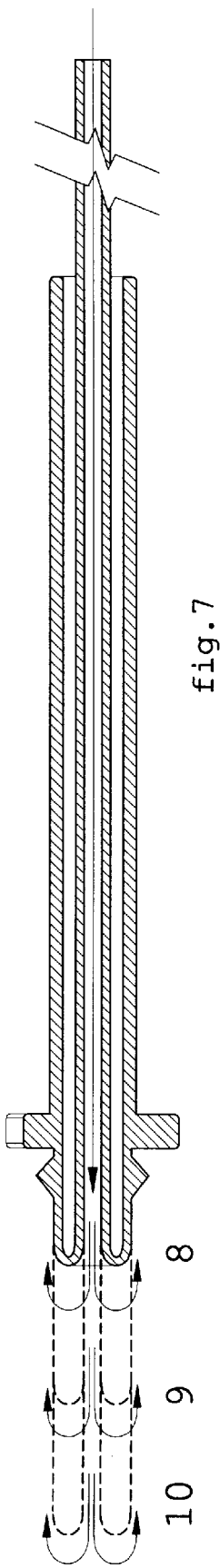

FIGS. 7 through 10 are longitudinal cross-sections of the device demonstrating the development of a double walled catheter from a single walled tube. Opening of the guide is seen between FIG. 7A and FIG. 8. Travel of the tube and growth of the catheter are indicated by arrows. The tines of the guide open passively as fabric from the inner tube becomes fabric of the outer tube.

FIG. 11 demonstrates the entry portal for a urine specimen.

The entire device is formed from a single extrusion molding of PTFE, in its preferred manufacture.

Alternate construction materials do exist and include (but are not limited to) elastomer, polyethylene, high slip polyethylene and Nylon. Multiple piece construction may be substituted for single piece construction. Areas of tube can selectively be affected by exposure to heat or chemicals, bringing about changes in flexibility.

The device is marketed in a sterile package and is disposable.

OPERATION OF INVENTION

The adult female patient is placed in a usual position for catheterization. Her legs are flexed and abducted at the hips. She may be up in stirrups or lying on a bed or examining table.

The operator wears a pair of clean gloves. Sterile gloves are not necessary. The gloves are for his own protection and to prevent carrying organisms from patient to patient. There is minimal risk that he could contaminate the system.

The operator next wipes the lower urethra with a milking motion downward along the lower vagina. He uses a single sweep with a cotton ball soaked in mild disinfectant. This is to remove any gathered mucous or fluid which might be present.

The operator then grasps handle 26 and aims its long axis to coincide with the long axis of the patient's urethra. His visualization may be improved by retracting the soft flesh lateral to the urethra in an anterior and lateral direction.

He now gently insinuates the collapsed tines of guide 22 into mucosal folds surrounding the urethral meatus. For this he uses a small circular motion. (Page 3 of drawings FIG. 7A).

Next he begins moving free tube 28 into the handle of the device. After grasping the tube between the fingers the free tube can be pushed into the cavity of the handle.

Advance by the tube causes a flower like opening of guide 22 and enables penetration of the urethra. Each tine functions as a small retractor of redundant mucosal tissue folds. Further advance of the free tube causes a double walled catheter to begin forming. Excessive urethral penetration is prevented by guard 24.

Finally a growing double walled catheter penetrates the internal urethral sphincter and urine flows through a sterile conduit into the waiting laboratory container. This container may be either sterile or non-sterile at the attending physicians' option. Not all catheterized specimens receive bacteriologic culture.

Conclusion, Ramifications, and Scope of Invention

Thus the reader will see that this invention provides a reliable, safe, yet economical device for gaining access to bladder urine.

This device permits economy in both the amount of supplemental equipment required and the level of operator training needed. Yet it performs without contamination of the bladder or of the urine specimen.

While my above description contains many specificities, these should not be construed as limitations on the scope of the invention, but rather as an exemplification of one preferred embodiment thereof.

Many other variations are possible. For example, the stated dimensions are appropriate to an adult female urethra. Those dimensions must all be changed to accommodate pediatric or male patients.

A host of alternate construction materials exists. A change of construction material will alter the flexibility and sliding features of both handle and tube. Some substitutes may require that the inner tube now be lubricated or tapered.

Lubrication of the exterior of the device may lead to bladder contamination and should be avoided. Flexibility of the tube can be further changed by changing its diameter or the thickness of its wall.

Multiple piece construction can also be substituted for the single piece construction method. While this change would complicate manufacture, it would permit a more diverse selection of materials to be used. Guard and handle shapes may vary within a broad range of additional designs.

Thus the scope of the invention should be determined by the appended claims and their legal equivalents rather than by the examples given.

I claim:

1. A medical device for sterile access to bladder urine comprising:

a rigid hollow handle forming an outer tube and having a length and a cavity extending therethrough;

a flexible cylindrical hollow tube extending through said handle forming an inner tube, said hollow tube having opposing first and second ends, said first end comprising a specimen exit end and said second end comprising a specimen entrance end, said specimen exit end extending beyond the length of said handle forming a free tube, said specimen entrance end comprising a junction between said inner and said outer tubes;

a guard surrounding said outer tube proximate said specimen entrance end;

and a guide comprising a plurality of radially positioned tines encircling said outer tube adjacent said guard, said tines having pointed ends whereby as the free tube is advanced through said cavity toward the specimen entrance end, said free tube becomes said inner tube to form a double walled catheter.

\* \* \* \* \*